United States Patent
Raines

Patent Number: 5,897,561
Date of Patent: Apr. 27, 1999

[54] CORING DEVICE

[76] Inventor: Edward P. Raines, 1500 S. 48th St., Suite 800, Lincoln, Nebr. 68506

[21] Appl. No.: 09/000,910

[22] Filed: Dec. 30, 1997

[51] Int. Cl.⁶ .............................. A61F 11/00; A61B 17/32
[52] U.S. Cl. ............................................ 606/108; 606/167
[58] Field of Search ................................ 606/1, 108, 167, 606/170, 180, 184, 185; 30/113.1, 113.2

[56] References Cited

U.S. PATENT DOCUMENTS

| | | |
|---|---|---|
| D. 266,871 | 11/1982 | Child . |
| 4,580,560 | 4/1986 | Straith . |
| 4,617,929 | 10/1986 | Gill . |
| 4,694,826 | 9/1987 | Chester . |
| 4,732,152 | 3/1988 | Wallsten et al. . |
| 4,768,507 | 9/1988 | Fischell et al. . |
| 4,955,890 | 9/1990 | Yamamoto et al. ..................... 606/108 |
| 5,026,377 | 6/1991 | Burton et al. ............................. 606/108 |
| 5,071,408 | 12/1991 | Ahmed .................................... 606/108 |
| 5,234,438 | 8/1993 | Semrad .................................... 606/108 |
| 5,290,295 | 3/1994 | Querals et al. .......................... 606/108 |
| 5,411,507 | 5/1995 | Heckele ................................... 606/108 |

*Primary Examiner*—Glenn K. Dawson
*Attorney, Agent, or Firm*—Zarley, McKee, Thomte, Voorhees & Sease; Dennis L. Thomte

[57] ABSTRACT

A coring device includes a semi-cylindrical channel with an angled forward end having a cutting edge thereon, with a second semi-cylindrical channel hinged to the cutting channel to pivot between a closed position forming a tube, and an open position permitting the introduction of a driveline between the channels. The second channel is shorter than the first channel, so that the cutting edge of the first channel projects forwardly beyond the second channel.

15 Claims, 2 Drawing Sheets

CORING DEVICE

TECHNICAL FIELD

The present invention relates generally to an apparatus for removing a cylindrical core from an object, and more particularly to a coring device for removing a pneumatic driveline from a patient.

BACKGROUND OF THE INVENTION

A pneumatic driveline is installed through the body wall of a patient at the time of implant of either a total mechanical artificial heart or a ventricular assist device. Obviously, this driveline provides the power for operating the particular device implanted in the patient.

At the time of explant of the device, the driveline can be very difficult to remove, since tissue of the body wall will grow around and on to the driveline. Currently, there is no simple and efficient method or apparatus for removing the driveline, and conventionally involves manually cutting around the tubular driveline with a scalpel.

SUMMARY OF THE INVENTION

It is therefore a general object of the present invention to provide an improved apparatus for removing a tubular driveline from a patient.

Another object is to provide a coring apparatus which is simple to use and economical to manufacture.

These and other objects of the present invention will be apparent to those skilled in the art.

The coring device of the present invention includes a semi-cylindrical channel with an angled forward end having a cutting edge thereon, with a second semicylindrical channel hinged to the cutting channel to pivot between a closed position forming a tube, and an open position permitting the introduction of a driveline between the channels. The second channel is shorter than the first channel, so that the cutting edge of the first channel projects forwardly beyond the second channel. The second channel provides a gripping surface for rotating the coring device around a driveline to cut the driveline free of a body wall.

DESCRIPTION OF THE PREFERRED EMBODIMENT

Figure 1:
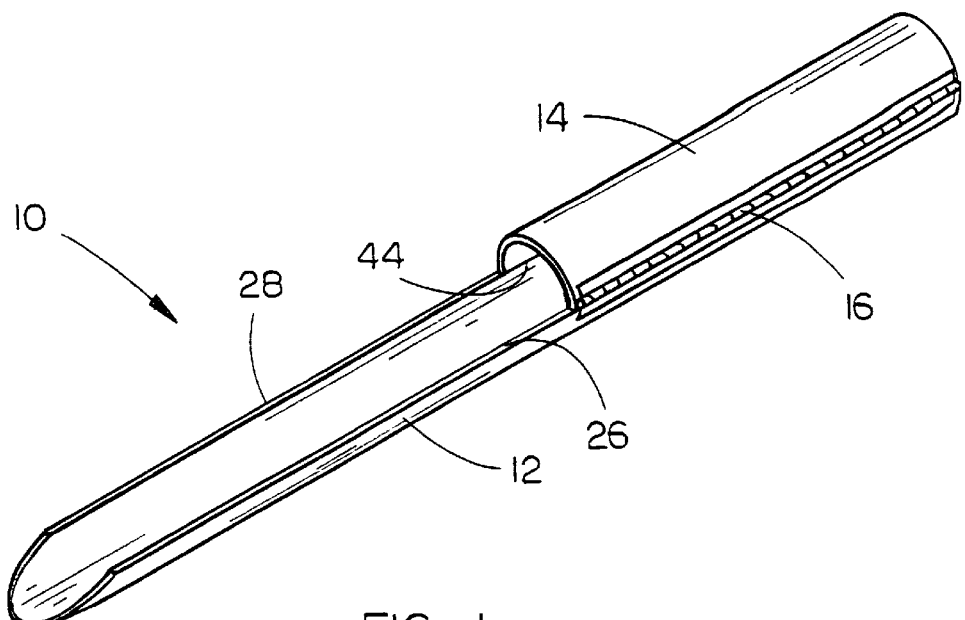
FIG. 1 is a perspective view of the coring device of the present invention.

Referring now to the drawings, in which similar or corresponding parts are identified with the same reference numeral and more particularly to FIG. 1, the coring device of the present invention is designated generally at 10 and includes three main components: a cutting channel 12, a gripping channel 14, and a hinge 16. Cutting channel 12 is an elongated semi-cylindrical member preferably formed of stainless steel, or other sterilizable material. In the alternative, the entire coring device 10 could be formed of a material which permits only a single use, thereby requiring replacement after a procedure.

Figure 2:
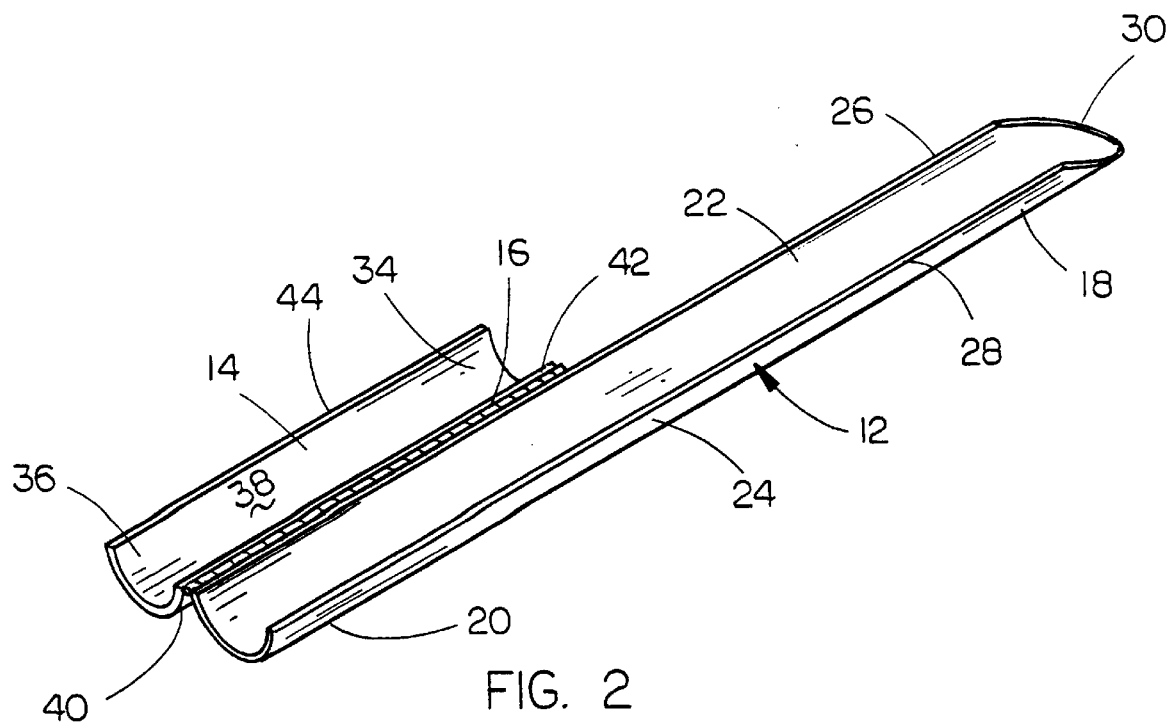
FIG. 2 is a perspective view of the coring device, in an "open" position.

Referring now to FIG. 2, it can be seen that cutting channel 12 has forward and rearward ends 18 and 20, respectively, inward and outward surfaces 22 and 24, respectively, and opposing side wall edges 26 and 28, respectively. The forward end 18 is cut at an angle rearwardly from the centerline of the channel to the edges 26 and 28 to form a cutting edge 30. The angle of the cutting edge is not believed to be critical, but is shown at approximately 45 degrees from a plane orthogonal to the longitudinal axis of the cutting channel 12.

Figure 4:
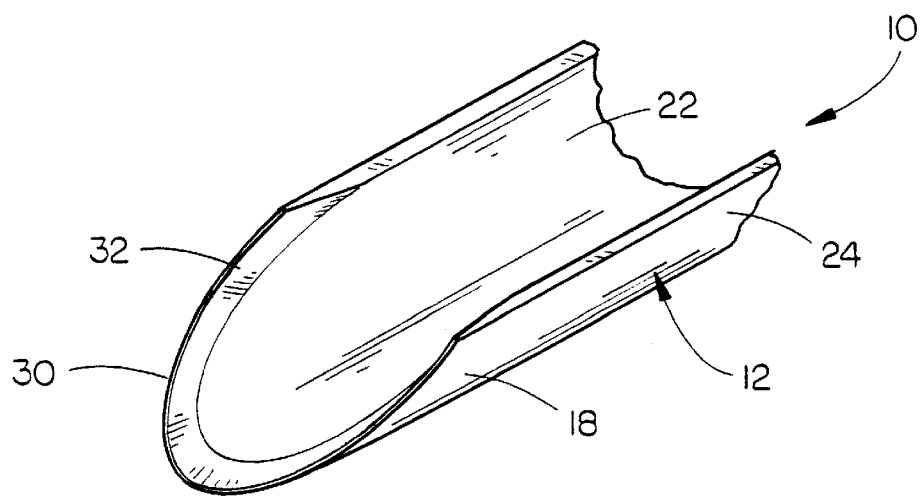
FIG. 4 is an enlarged perspective view of the forward, cutting end of the coring device.

FIG. 4 shows a more detailed depiction of the cutting edge 30 at the forward end 18 of coring device 10. Cutting edge 30 is preferably sharpened to a razor-edge by beveling the forward end 18 inwardly from the outward surface 24 to the inward surface 22, along the entire length of the cutting edge 30. While this is the preferred embodiment of the cutting edge 30, other beveling arrangements would give equivalent results. For example, the bevel could be formed outwardly from the inward surface to the outward surface. In addition, both the inward and outward surfaces could be beveled to form a cutting edge located generally centrally between the inward and outward surfaces. In addition, the thickness of the wall of the cutting channel 12 could be thin enough that no beveling is needed.

Referring once again to FIG. 2, gripping channel 14 is also a semi-cylindrical member having forward and rearward ends 34 and 36, respectively, inward and outward surfaces 38 and 40, respectively, and opposing side wall edges 42 and 44, respectively. Gripping channel 14 has a radius equal to that of the cutting channel 12. Hinge 16 is a continuous hinge, and extends along the length of gripping channel side wall edge 42 to pivotally connect the gripping channel to the cutting channel. hinge 16 is attached to cutting channel 12 along side wall edge 26 and extends forwardly from the rearward end 20. It can be seen that gripping channel 14 may be pivoted to form a cylindrical tube with the cutting channel, with cutting channel edges 26 and 28 in contact with gripping channel edges 42 and 44, respectively, as shown in FIG. 1.

Figure 3:
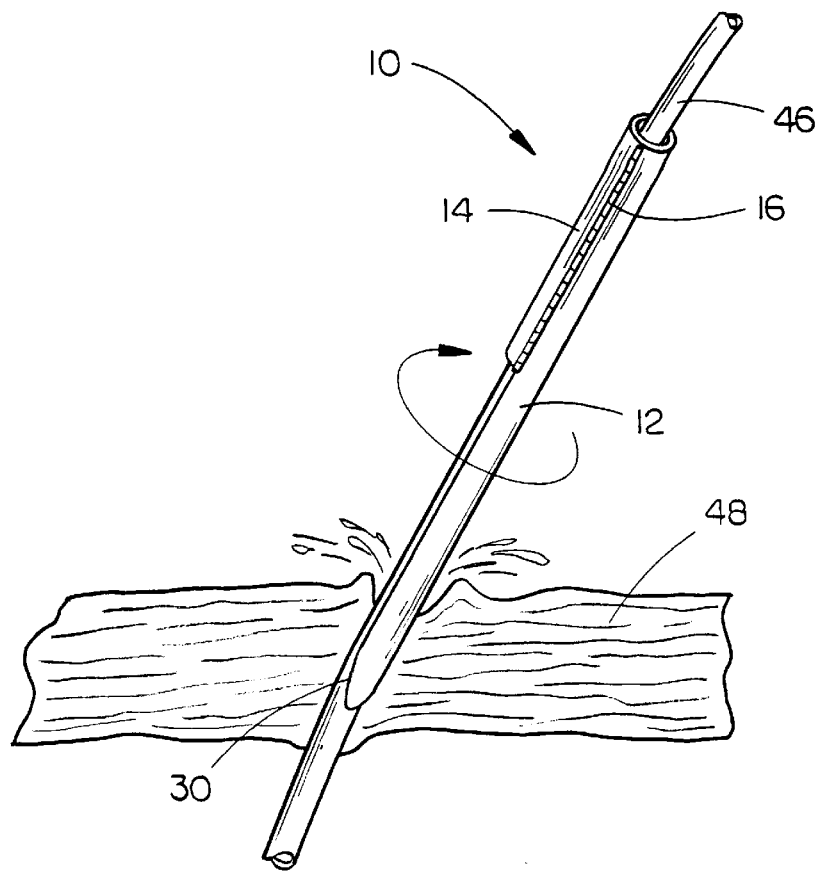
FIG. 3 is a perspective view showing the coring device in use, with a portion of a body wall shown in cross-section.

In use, coring device 10 is first opened, by pivoting gripping channel 14 away from cutting channel 12, as shown in FIG. 2. This permits cutting channel 12 to be positioned adjacent the pneumatic driveline 46, shown in FIG. 3, with the tubular driveline 46 positioned within the cutting channel 12 and coaxial therewith. Channels 12 and 14 have radii slightly greater than that of driveline 46 so that gripping channel 14 may be pivoted to the "closed" position shown in FIG. 3, and thereby completely surround driveline 46.

Once coring device 10 has been closed around driveline 46 the device may be rotated about its longitudinal axis, around driveline 46, and moved downwardly along the driveline until cutting edge 30 engages the body wall. Because the cutting edge 30 is semi-cylindrical, it will cleanly cut the tissue around the driveline, yet remain in very close proximity to the driveline. This permits the surgeon to make a small, clean incision around the driveline 46, with the driveline actually acting as a "guide" for the coring device as it proceeds through the body wall 48. The gripping channel 14 provides a grip for the hand to rotate the device around the driveline, while hinge 16 permits the device 10 to be easily attached and removed from the driveline.

Whereas the invention has been shown and described in connection with the preferred embodiment thereof, many modifications, substitutions and additions may be made which are within the intended broad scope of the appended claims.

I claim:

1. A method for releasing a generally cylindrical member which is journaled through a body wall, comprising the steps of:
   providing a coring device having a first semi-cylindrical channel with a forward end and a cutting edge formed on the forward end;
   positioning the cutting edge against the body wall with the cylindrical member positioned within the channel; and
   rotating the channel around the cylindrical member while moving the channel downwardly through the body wall to form a generally cylindrical incision around the cylindrical member.

2. The method of claim 1, wherein the coring device includes a second channel pivotally connected to the first channel for movement between a closed position forming a cylindrical tube surrounding the circumference of the cylindrical member, and an open position permitting entry and removal of the cylindrical member from the channels, and further comprising the step of moving the second channel to the open position and thence to the closed position enclosing the cylindrical member between the channels, prior to the positioning step.

3. A surgical tool, comprising:
   a first elongated, generally semi-cylindrical channel having a forward end and a rearward end, the forward end having a cutting edge formed thereon; and
   a second elongated, generally semi-cylindrical channel having a forward end and a rearward end, pivotally connected to the first channel for pivotal movement between a closed position forming a cylindrical tube with the first channel, and an open position revealing inward surfaces of the channels;
   said second channel having a length as measured from its forward end to its rearward end, less than the length of said first channel;
   said second channel being pivotally connected to said first channel at the rearward end of said first channel, such that the forward end of said first channel projects forwardly beyond the forward end of said second channel.

4. The tool of claim 3, further comprising a hinge mounted on the rearward end of the first channel and mounted to the second channel, for pivotally connecting the channels.

5. The tool of claim 4, wherein said first channel includes opposing side wall edges extending along its length, and wherein said second channel includes opposing side wall edges extending along its length, and wherein the channels are pivotally connected along a pivotal axis parallel to longitudinal axes of the channels and proximal and parallel to one side wall edge of each channel.

6. The tool of claim 5, wherein the forward end of the first channel has a forward edge formed at an angle which slopes rearwardly from a central portion of the first channel to the opposing side wall edges, said cutting edge being formed along the angled forward edge.

7. The tool of claim 6, wherein the cutting edge is beveled to form a sharp edge.

8. The tool of claim 7, wherein the cutting edge is beveled from an exterior surface inwardly to an interior surface, along the entire cutting edge.

9. The tool of claim 8, wherein said channels and hinge are formed from sterilizable materials.

10. A surgical tool, comprising:
    a first elongated, generally semi-cylindrical channel having a forward end and a rearward end, the forward end having a cutting edge formed thereon; and
    a second elongated, generally semi-cylindrical channel having a forward end and a rearward end, pivotally connected to the first channel for pivotal movement between a closed position forming a cylindrical tube with the first channel, and an open position revealing inward surfaces of the channels;
    said first channel including opposing side wall edges extending along its length;
    said second channel including opposing side wall edges extending along its length, and wherein the channels are pivotally connected along a pivotal axis parallel to longitudinal axes of the channels and proximal and parallel to one side wall edge of each channel.

11. The tool of claim 10, wherein the forward end of the first channel has a forward edge formed at an angle which slopes rearwardly from a central portion of the first channel to the opposing side wall edges, said cutting edge being formed along the angled forward edge.

12. The tool of claim 11, wherein the cutting edge is beveled to form a sharp edge.

13. The tool of claim 11, wherein the cutting edge is beveled from an exterior surface inwardly to an interior surface, along the entire cutting edge.

14. A coring device for releasing a pneumatic driveline journaled through a body wall, comprising:
    a first elongated, generally semi-cylindrical channel having a forward end and a rearward end, the forward end having a cutting edge formed thereon; and
    a second elongated, generally semi-cylindrical channel having a forward end and a rearward end, pivotally connected to the first channel for pivotal movement between a closed position forming a cylindrical tube with the first channel, and an open position revealing inward surfaces of the channels;
    said second channel having a length, as measured from its forward to its rearward end, less than the length of the first channel;
    said second channel being pivotally connected to the first channel at the rearward end of the first channel, such that the forward end of the first channel projects forwardly beyond the forward end of the second channel;
    said first channel including opposing side wall edges extending along its length;
    said second channel including opposing side wall edges extending along its length;
    said channels being pivotally connected along a pivotal axis parallel to longitudinal axes of the channels and proximal and parallel to one side wall edge of each channel.

15. The coring device of claim 14, wherein the forward end of the first channel has a forward edge formed at an angle which slopes rearwardly from a central portion of the channel to the opposing side wall edges, said cutting edge being formed along the angled forward edge.

* * * * *